United States Patent [19]

Kotani et al.

[11] 4,016,419

[45] Apr. 5, 1977

[54] NON-DISPERSIVE X-RAY FLUORESCENCE ANALYZER

[75] Inventors: Haruo Kotani, Osaka; Haruyoshi Hirata; Yoshinori Hosokawa, both of Kyoto, all of Japan

[73] Assignee: Horiba, Ltd., Kyoto, Japan

[22] Filed: Aug. 26, 1975

[21] Appl. No.: 607,903

[30] Foreign Application Priority Data

Sept. 30, 1974 Japan .................. 49-113115

[52] U.S. Cl. ............................. 250/272; 250/273
[51] Int. Cl.² ...................................... G01N 25/00
[58] Field of Search ........... 250/272, 273, 274, 252

[56] References Cited

UNITED STATES PATENTS

| | | | |
|---|---|---|---|
| 2,763,784 | 9/1956 | Webster | 250/273 |
| 2,784,319 | 3/1957 | Flook et al. | 250/273 |
| 2,890,344 | 6/1959 | Behr | 250/273 |
| 3,114,832 | 12/1963 | Alvarez | 250/272 |
| 3,859,525 | 1/1975 | Ashe | 250/272 |

Primary Examiner—Alfred E. Smith
Assistant Examiner—B. C. Anderson
Attorney, Agent, or Firm—Wenderoth, Lind & Ponack

[57] ABSTRACT

A non-dispersive fluorescence x-ray analyzer apparatus and method for measuring the concentration of an element contained in a sample. The apparatus has an x-ray source which directs x-rays against a sample to be analyzed and a reference sample which are both at equal distances from the x-ray source. The fluorescence x-ray spectrum from both the sample to be analyzed and the reference sample is detected and converted into a series of pulse signals. Counters count the signals from both samples, and the counter for counting the pulse signals from the reference sample is set to terminate the operation of the counter for counting the signals from the sample when a pre-determined number of pulses is counted from the reference sample. The number of pulses from the sample to be analyzed is then used for performing a mathematical computation to determine the concentration of the element in the sample being analyzed, which concentration is proportional to the number of pulses counted.

3 Claims, 5 Drawing Figures

NON-DISPERSIVE X-RAY FLUORESCENCE ANALYZER

DETAILED DESCRIPTION OF THE INVENTION

BACKGROUND OF THE INVENTION

For the analysis of elements contained in various substances, various analytical methods using analyzers especially for the purpose of analysis have been developed. Among them, as it is well-known, fluorescence X-ray analysis has been widely used in various fields since the analysis by this method can be carried out without destroying the substance to be analysed.

Fluorescence X-ray analysis is a method of elemental analysis to identify each element contained in a substance to be analysed from the characteristic wave length of the fluorescence X-rays radiated from the substance when the substance is excited by irradiation by X-rays emitted from an excited target of an X-ray tube (every element radiates a fluorescence X-ray having a characteristic wave length) and more over, to determine the amount of the element from the intensity of the said characteristic spectrum. The method of fluorescence X-ray analysis can be classified into two systems, that is, the one is a dispersion system and the other is a nondispersion system. The dispersion system carries out the measurement of the said characteristic spectrum by a detector detecting the radiated fluorescence X-rays by a spectroscope (diffraction crystal, etc.). On the other hand, the non-dispersion system measures the characteristic spectrum directly from the fluorescence X-rays using a balanced filter without using a spectroscope or measures the spectrum directly by a detector of semiconductor material utilizing its superior ability to distinguish the emission energies of the fluorescence spectra.

The present invention relates to a non-dispersive fluorescence X-ray analyzer belonging to the latter system described above.

SUMMARY OF THE INVENTION

The present invention provides a non-dispersive fluorescence X-ray analyzer which can determine the content of a sample with a high accuracy, since the analyzer controls the quantity of X-rays irradiated to the sample so that it has a definite value, regardless of any drift of the intensity of the irradiated X-rays emitted from an X-ray tube due to a drift of a high voltage power source or to a change of the temperature of the atmosphere from the window of the X-ray tube to the sample.

BRIEF DESCRIPTION OF THE DRAWINGS

The attached drawings show an embodiment of the present invention, wherein.

DETAILED DESCRIPTION OF THE PREFERRED EMBODIMENT

Figure 1:
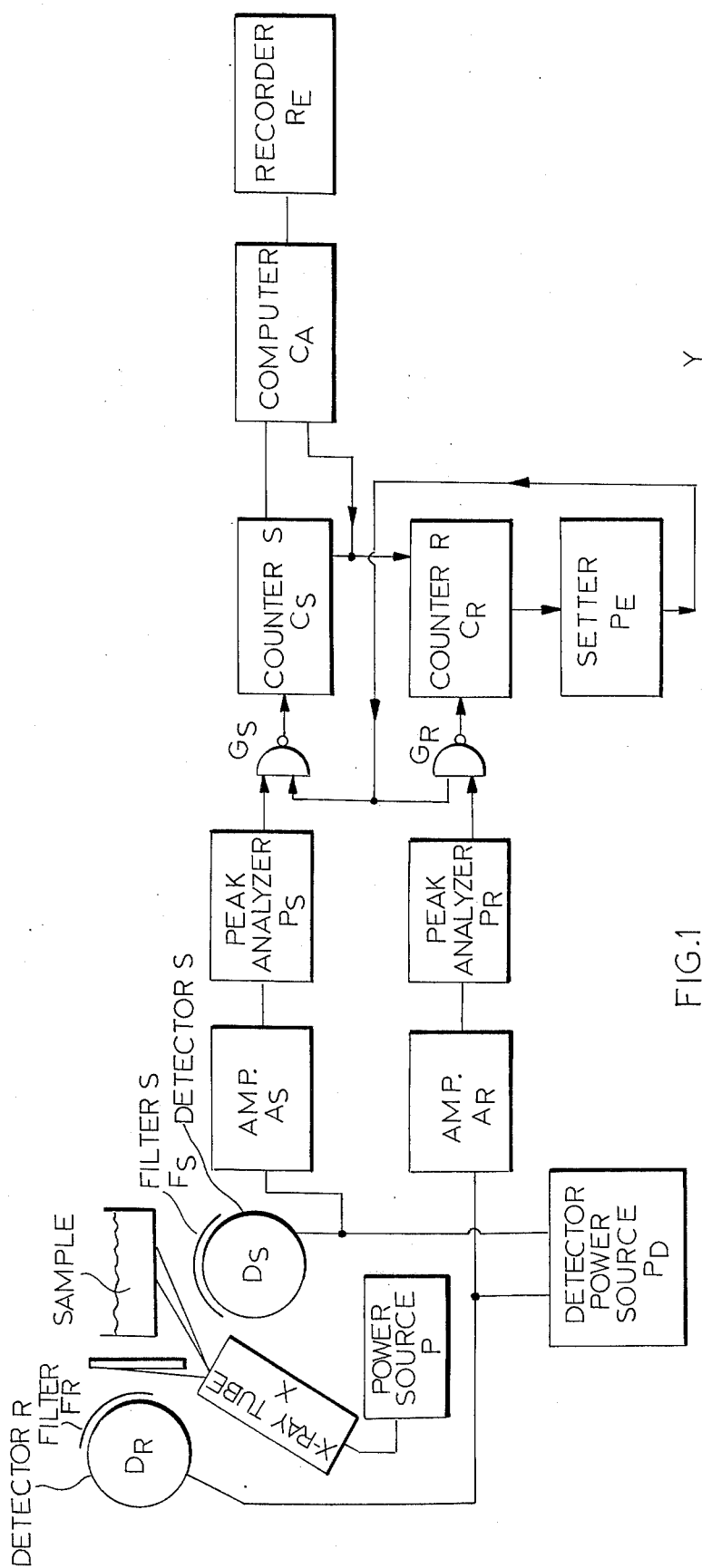
FIG. 1 is a block diagram showing the whole system.

In the system of FIG. 1, an X-ray tube X is excited by a high voltage power source P and irradiates X-rays to a sample S to be analysed and to a reference sample R, the distance between the X-ray tube X and the sample S and the distance between the X-ray tube X and the reference sample R being exactly equal to each other, so as to carry out the measurement with a high accuracy by having both samples irradiated under the same conditions with respect to the absorption and the scattering of X-rays during the passage from window of the X-ray tube X to each sample. $D_S$ and $D_R$ are X-ray detectors, which detect fluorescence X-rays from both samples S and R respectively and convert the detected results into pulse signals.

The distance between the detector Ds and the sample S and the distance between the detector Dr and the sample R are made exactly equal so that the same atmospheric conditions exist within those regions; that is, by insuring that the same conditions exist for the absorption and scattering of fluorescence X-rays from both samples S and R, it becomes possible to make a measurement with high accuracy.

Further, by a proper choice of materials for filters $F_s$ and $F_R$ fitted on the corresponding detectors $D_S$ and $D_R$ and of the target material of the X-ray tube X and a proper setting of the supplied voltage and current density from the high voltage power source P, the analyzer of the present invention is be able to detect most effectively by the detectors $D_S$ and $D_R$ only the fluorescence X-ray spectrum showing the concentration of the element which is the object of the analysis, among various spectra of fluorescence X-rays radiated from the sample S and R. For an example, in case the object of the analysis is sulphur, a proportional counter is used for the detectors $D_S$ and $D_R$, the target material is titanium, the applied voltage is 8 KV and the current is 150 MA.

Electric pulse signals transmitted from the detectors $D_S$ and $D_R$ are amplified by well-known pulse amplifiers $A_S$ and $A_R$, then, only the pulse signals corresponding to the fluorescence X-rays of the element for which the analysis is being made are selected from among the various pulses by conventional pulse height analyzers $P_S$ and $P_R$ and the selected pulse signals are introduced into a pair of conventional counters $C_S$ and $C_R$ through gate circuits $G_S$ and $G_R$, respectively, which count each number of pulses.

The counter $C_R$ is connected with a setter $P_E$, and when the number of count of pulse signals obtained by the counter $C_R$ becomes equal to that preliminary set in it, gate circuits $G_S$ and $G_R$ are closed by a signal sent from the said setter $P_E$. The counter $C_S$ which is provided on the sample-side is connected with a computer $C_A$ which can read the out-put signals from the counter $C_S$, execute a mathematical computation and memorize its result. The said computer $C_A$ carries out a mathematical computation using the out-put signals from the counter $C_S$ and the concentration of the element is finally determined thereby.

Further, $R_E$ shown in FIG. 1 is an apparatus to indicate or record the concentration of the element which is the object of the analysis contained in the sample S and $P_D$ is a high voltage power source for the detectors.

In the following, the method of determining the concentration of the element which is the object of the analysis, using the said non-dispersive fluorescence X-ray analyzer of the present invention will be explained, the method explained in the following being the most effective way for the measuring.

In general, in a range of low concentration or in a short range even if the concentration if high, there is linear relation between the concentration of the element and the count obtained by the counter $C_S$. (For example, FIGS. 2a, 2b and 2c show linear relations between the concentrations of tin, copper and molybdenum, respectively, chosen as objects of the analysis, and the count obtained therefrom.)

Figure 2A:
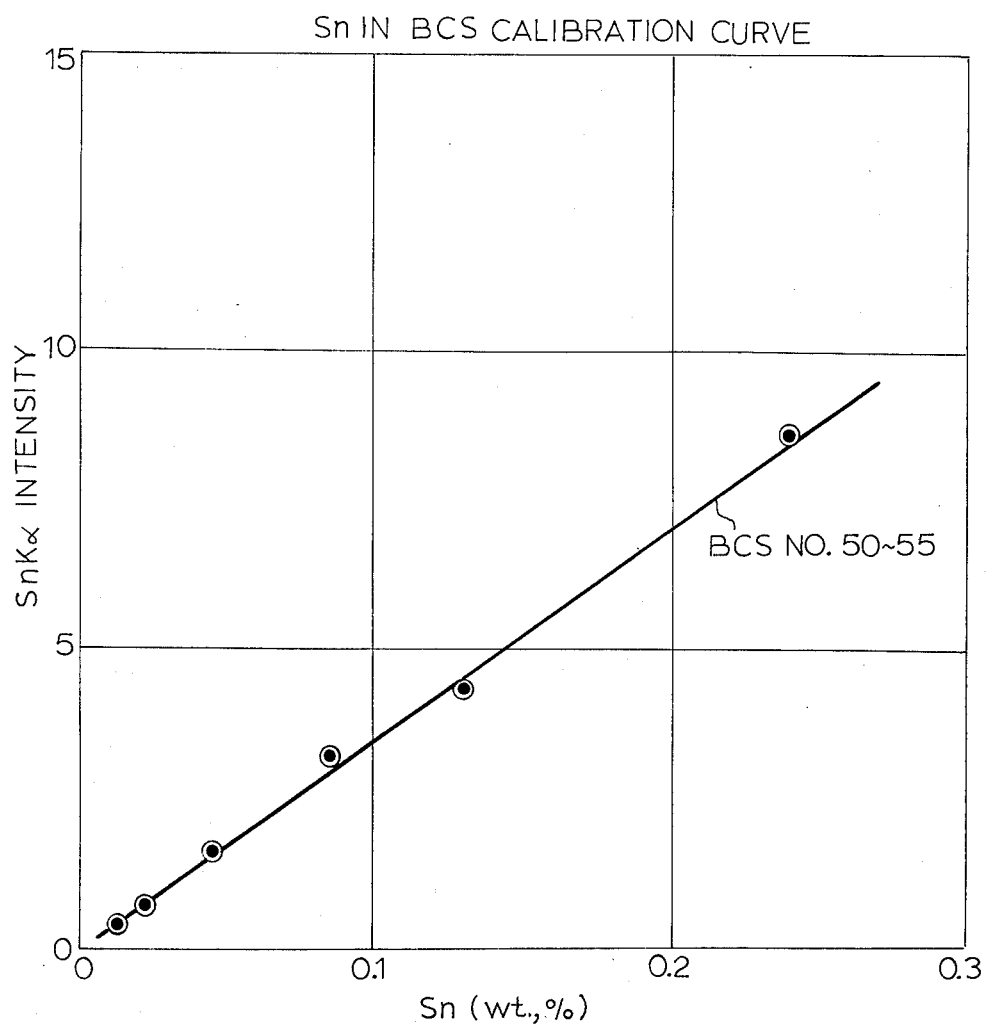
FIG. 2a–2c are graphs showing the relation between the concentration of the element and the count.
Figure 2B:
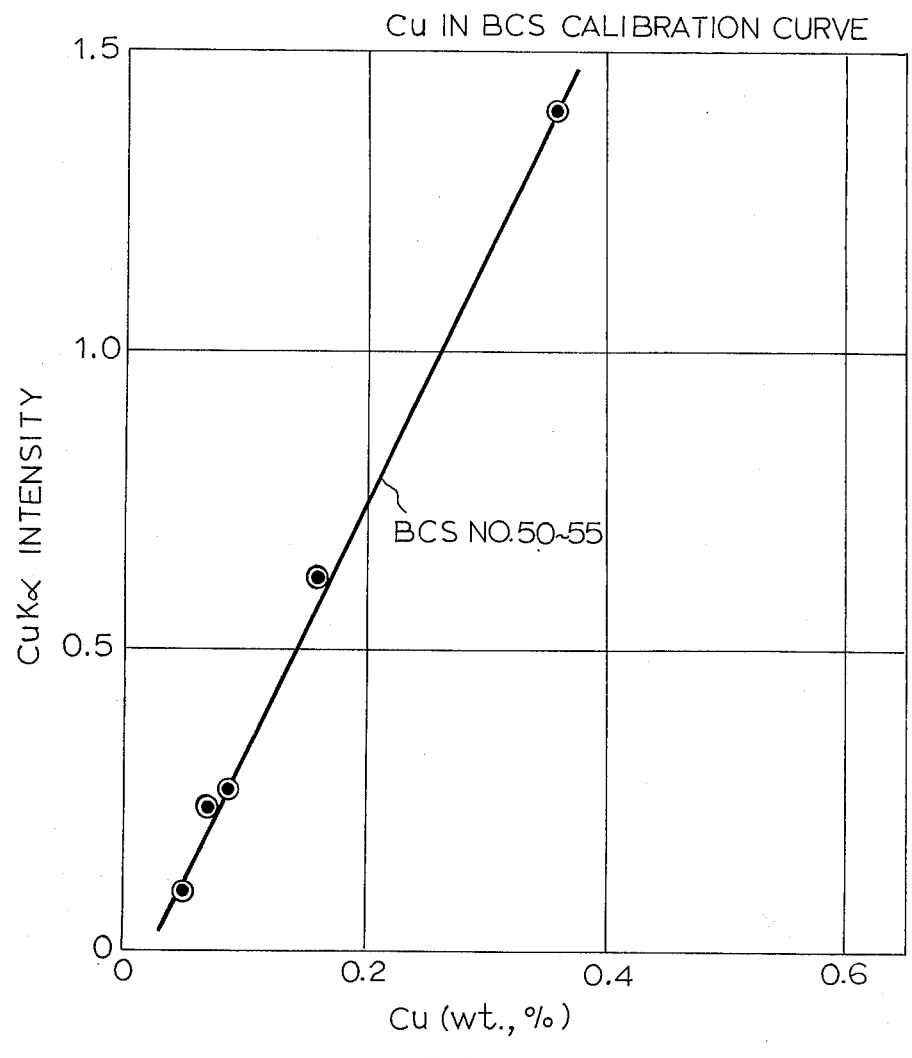
Figure 2C:
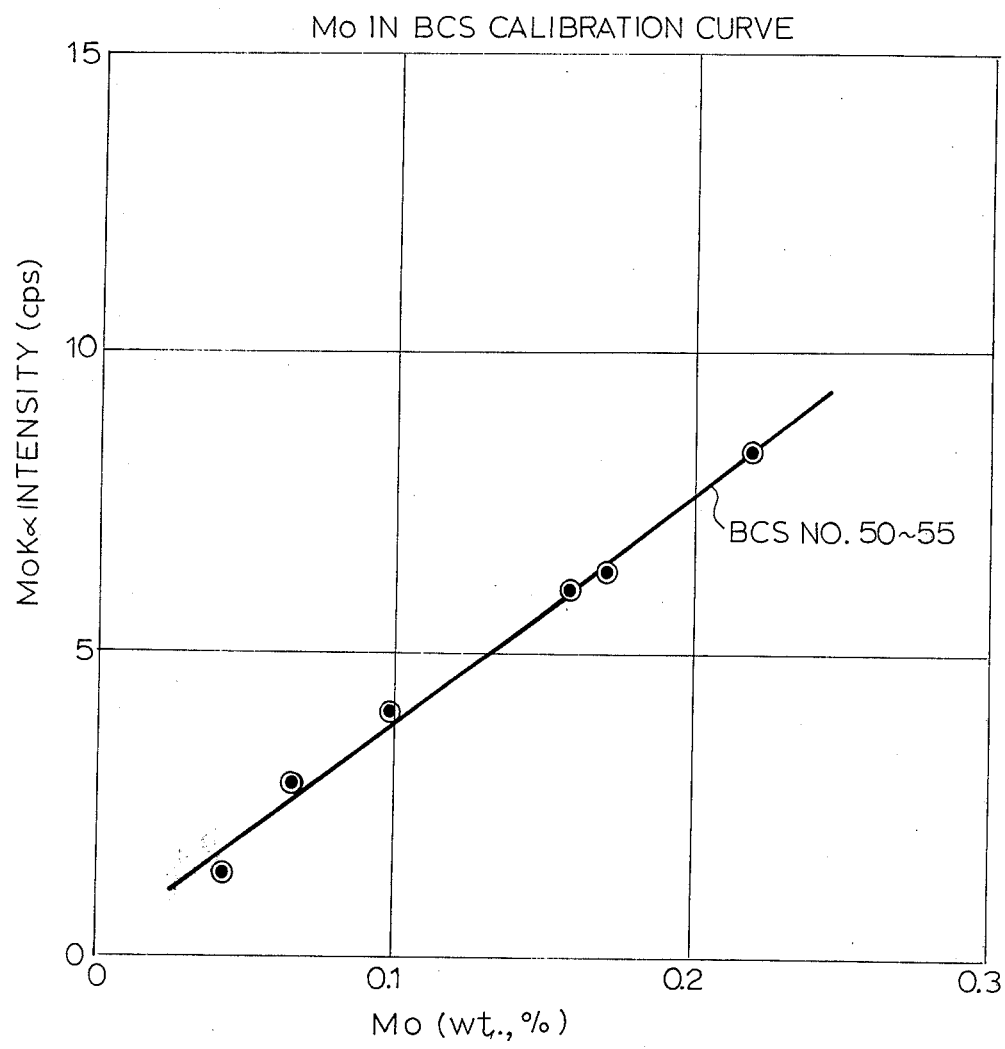

That is, as is clearly understood from FIGS. 2a–2c if the concentration is denoted as y and the count is denoted as x, the following linear relation exits between $y$ and $x$.

$$y = ax + b \qquad (1)$$

Figure 3:
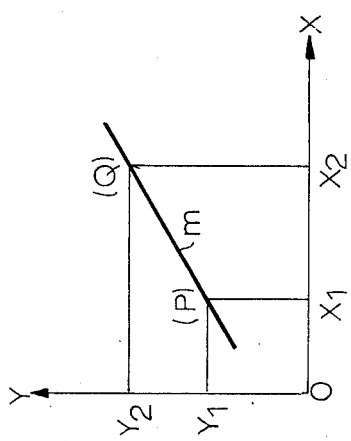
FIG. 3 is a graph showing a method of measurement of the concentration using the non-dispersive fluorescence X-ray analyzer of the present invention.

Here, it is necessary to find the values of $a$ and $b$, experimentally and this can be done as follows. Before a practical analysis operation, two standard samples the concentrations of which are known as $y_1$ and $y_2$, are analyzed using the said analyzer to obtain the corresponding counts $x_1$ and $x_2$ the counter $C_S$. Putting the known values of $y_1$ and $y_2$ and the corresponding observed values of $x_1$ and $x_2$ into the said computer $C_A$ and executing a mathematical computation, the computer is caused to memorize the thus obtained linear relation $m$ (calibration curve) which is a straight line passing through two points $(x_1, y_1)$ and $(x_2, y_2)$ as shown in FIG. 3, corresponding to the linear relations shown in FIGS. 2a–2c. Or in other words, using the said computer $C_A$, simultaneous equations consisting of $$y_1 = ax_1 + b \qquad (2)$$

$$y_2 = ax_2 + b \qquad (3)$$

wherein the equation (2) is derived from the linear relation between the concentration $y_1$ and the count $x_1$ for the one of the two standard samples and the equation (3) is derived from the same linear relation between the concentration $y_2$ and the count $x_2$ the other standard sample, are solved and the obtained values of $a$ and $b$ are memorized by the computer.

In the next step, an analysis is carried out on a sample in which the concentration of the element is not known, using the said analyzer. Then, the count $x$ counted by the counter $C_S$ is put into the computer $C_A$ and the concentration $y$ is automatically calculated by the computer based upon the equation (1) and the concentration y of the element which is the object of the analysis in the sample is indicated or recorded by the indicator or recorder. $R_E$.

Furthermore, it can be pointed out that in the said fluorescence X-ray analyzer having the construction described above, when the number of pulses counted by the counter R inserted into the reference sample side becomes equal to that preliminary set, the supply of pulse signals to the counter S of the sample side is automatically stopped and the concentration of the element for which the sample is being analyzed is determined from the count obtained by the counter S of the sample side. Accordingly, regardless of the existence of any drifts, for example, such as a drift of intensity of irradiated X-rays from the X-ray tube, a drift of the said high voltage power source P or a drift of temperature of the atmosphere from the window of the X-ray tube to each sample S or R, the non-dispersive fluorescence X-ray analyzer of the present invention is able to carry out the elemental analysis with a very high accuracy by the measurement of the quantity of fluorescence X-rays radiated from the sample under control of the quantity of X-rays irradiated onto the sample without any disturbance from those drifts such as the drift of intensity of the irradiated X-rays, etc. described above.

In the present invention, since various factors which cause experimental errors are offset completely, it is possible to carry out an analysis with high accuracy and, moreover, by the conbination with a computer, it becomes possible to measure directly the concentration of any element which is the object of analysis, very accurately.

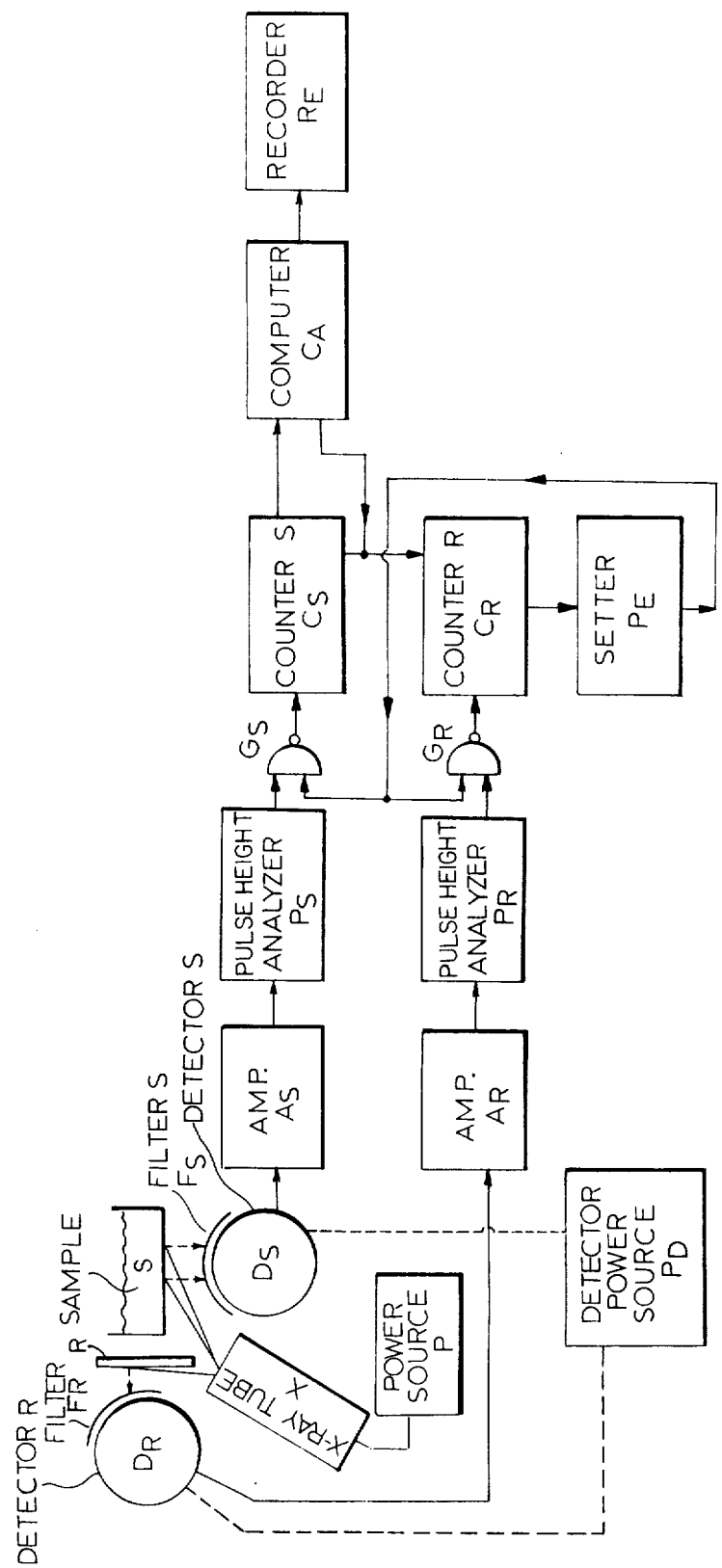

What is claimed is:

1. A non-dispersive fluorescence X-ray analyzer for measuring the concentration of an element contained in a sample, comprising an X-ray source including a power source, means for holding a sample to be analyzed and a reference sample in the path of the X-rays from said X-ray source, detecting means for each of said samples for detecting the fluorescence X-ray spectrum of the said element for which the analysis is being made from among the fluorescence X-ray spectra radiated from each sample and converting it to a series of pulse signals for each sample, a counting means connected to each detection means for counting the pulse signals from each sample, and means coupled between the respective counting means for stopping the supply of pulse signals to the counting means for the sample detecting means when the pulses counted by the counting means for the reference sample becomes equal to a predetermined number, whereby the number of pulses counted for the sample to be analyzed can be used for performing a mathematical computation to determine the concentration of the element for which the sample is being analyzed and whereby drifts of the intensity of the output of the X-ray source and drifts due to temperature changes, for example, are automatically compensated for.

2. A non-dispersive fluorescence X-ray analyzer as claimed in claim 1, wherein the distance from the said X-ray source to the sample to be analyzed and the distance from the said X-ray source to the reference sample are equal to each other, and the distance from the sample to be analyzed to the detection means for the sample to be analyzed and the distance from the reference sample to the detection means for the said reference sample are also equal to each other.

3. A non-dispersive fluorescence X-ray analysis method for measuring the concentration of an element contained in a sample, comprising directing X-rays from an X-ray source onto both a sample to be analyzed and a reference sample which are at the same distance from the X-ray source, detecting the fluorescence X-ray spectrum of the element for which the analysis is being made from among the fluorescence X-ray spectra radiated from each sample and converting it into a series of pulse signals for each sample, and in order to compensate for drifts of the intensity of the X-rays and drifts due to temperature changes, for example, counting the pulse signals from each sample and when the number of pulse signals from the reference sample has reached a predetermined number, stopping the counting of pulse signals from the sample to be analyzed, and calculating from the number of pulse signals counted for the sample to be analyzed the concentration of the element in the sample.

* * * * *

UNITED STATES PATENT OFFICE

CERTIFICATE OF CORRECTION

Patent No. 4,016,419   Dated April 5, 1977

Inventor(s) HARUO KOTANI, HARUYOSHI HIRATA and YOSHINORI HOSOKAWA

It is certified that error appears in the above-identified patent and that said Letters Patent are hereby corrected as shown below:

The drawing figure which appears on the cover sheet and figure 1 of the drawings should appear as shown on the attached sheet.

Signed and Sealed this

Tenth Day of October 1978

[SEAL]

Attest:

RUTH C. MASON
Attesting Officer

DONALD W. BANNER
Commissioner of Patents and Trademarks